(12) United States Patent
Roberts et al.

(10) Patent No.: US 11,161,129 B2
(45) Date of Patent: Nov. 2, 2021

(54) DEVICE AND METHOD FOR SPRAYING HOT WATER IN A FINE MIST TO WINDROWED ALFALFA HAY TO SIMULATE THE EFFECT OF DEW

(71) Applicant: Harvest Tec, Inc., Hudson, WI (US)

(72) Inventors: Jeffrey S. Roberts, Hudson, WI (US); Ryan P. Johnson, Somerset, WI (US)

(73) Assignee: Harvest Tec, Inc., Hudson, WI (US)

( * ) Notice: Subject to any disclaimer, the term of this patent is extended or adjusted under 35 U.S.C. 154(b) by 71 days.

(21) Appl. No.: 16/142,705

(22) Filed: Sep. 26, 2018

(65) Prior Publication Data

US 2019/0193097 A1 Jun. 27, 2019

Related U.S. Application Data

(60) Provisional application No. 62/563,112, filed on Sep. 26, 2017.

(51) Int. Cl.
| | |
|---|---|
| *B05B 9/03* | (2006.01) |
| *A61L 9/14* | (2006.01) |
| *A01F 29/01* | (2006.01) |
| *B05B 9/00* | (2006.01) |
| *B05B 12/12* | (2006.01) |
| *B05B 3/00* | (2006.01) |
| *B05B 3/02* | (2006.01) |
| *A23N 17/00* | (2006.01) |
| *A01D 87/12* | (2006.01) |
| *B05B 9/04* | (2006.01) |

(52) U.S. Cl.
CPC ............... *B05B 9/03* (2013.01); *A01F 29/01* (2013.01); *A23N 17/004* (2013.01); *A61L 9/14* (2013.01); *B05B 3/001* (2013.01); *B05B 3/027* (2013.01); *B05B 9/007* (2013.01); *B05B 12/124* (2013.01); *A01D 87/12* (2013.01); *B05B 9/002* (2013.01); *B05B 9/0403* (2013.01)

(58) Field of Classification Search
CPC ..... A01F 15/0816; A01D 84/00; A01D 43/14; A01D 78/00; A01D 78/02; B05B 3/027; B05B 3/001; B05B 9/002; B05B 9/007; B05B 9/04; B05B 9/0403
USPC ............. 239/135, 160, 162, 172, 225.1, 589
See application file for complete search history.

(56) References Cited

U.S. PATENT DOCUMENTS

| | | | | |
|---|---|---|---|---|
| 6,109,008 A | * | 8/2000 | Staheli | A01F 15/0816 56/10.2 B |
| 6,233,840 B1 | * | 5/2001 | Finney | A01D 84/00 239/171 |
| 2006/0283163 A1 | * | 12/2006 | Kraus | A01D 89/006 56/16.8 |

* cited by examiner

Primary Examiner — Christopher S Kim
(74) Attorney, Agent, or Firm — Skinner and Associates; Joel D. Skinner, Jr.

(57) ABSTRACT

An apparatus and method for simulating the effects of dew are disclosed. The apparatus includes a moveable platform; a rotatable base, the rotatable base being connected to the platform; and a plurality of elongated rods for penetrating and spraying beneath the surface of a windrow. The rods radiate from a longitudinal axis of the rotatable base.

13 Claims, 4 Drawing Sheets

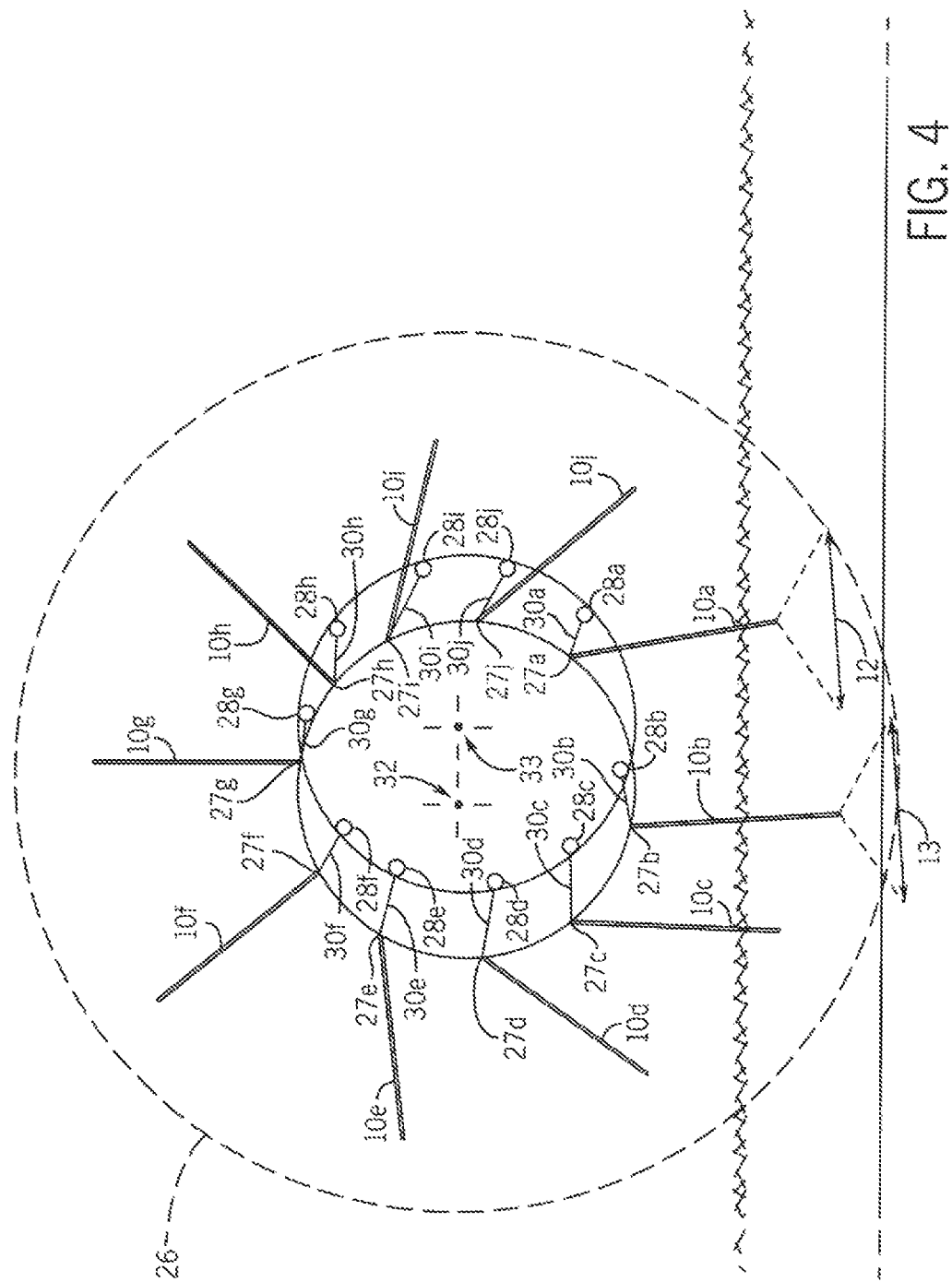

DEVICE AND METHOD FOR SPRAYING HOT WATER IN A FINE MIST TO WINDROWED ALFALFA HAY TO SIMULATE THE EFFECT OF DEW

CROSS-REFERENCE TO RELATED APPLICATIONS, IF ANY

This application claims the benefit under 35 U.S.C. 119(e) of U.S. Provisional Patent Application Ser. No. 62/563,112, filed Sep. 26, 2017, which is/are hereby incorporated by reference.

37 C.F.R. § 1.71(e) AUTHORIZATION

A portion of the disclosure of this patent document contains material which is subject to copyright protection. The copyright owner has no objection to the facsimile reproduction by anyone of the patent document or the patent disclosure, as it appears in the US Patent and Trademark Office patent file or records, but otherwise reserves all copyright rights whatsoever.

STATEMENT REGARDING FEDERALLY SPONSORED RESEARCH OR DEVELOPMENT

Not applicable.

REFERENCE TO A MICROFICHE APPENDIX, IF ANY

Not applicable.

BACKGROUND OF THE INVENTION

1. Field of the Invention

The present invention relates, generally, to agricultural systems, apparatus and methods. Particularly, the invention relates to system, apparatus and method of processing hay during baling. Most particularly, the invention relates to a system, apparatus and method of simulating the effect of dew in alfalfa hay during baling.

2. Background Information

Alfalfa hay is a major crop for the feeding of livestock. The most prevalent method of harvesting and handling alfalfa hay, is to cut the hay, lay it in windrows and let the natural elements (sun and wind) dry the alfalfa hay in the windrow down to a level of moisture that is acceptable for baling. The highest moisture level that is acceptable for baling is 18% moisture due to the occurrence of mold growth that can significantly reduce the feed quality. Most of the nutrients in alfalfa hay are in the leaf portion of the plant which by mass is 50% of the plant, but contains 90% of the usable nutrients for livestock. Below 13% moisture, the leaves will become brittle and shatter as the windrow is mechanically handled by the alfalfa hay baler resulting in a loss of quality and yield. Operating within this narrow band of moisture, 18% on top end and 13% on the low end poses operating challenges for the producers of alfalfa. A common method for harvesting alfalfa is to cut it and lay it in windrows, let to dry completely which would be below 13% moisture and then bale it when natural dew adds moisture to the alfalfa hay. When conditions for dew to form occur, the windrow can easily gain 2 to 4 points of moisture within a short period of time, bringing it up to a moisture where the leaves do not shatter off. As the dew increases, the alfalfa hay can pick up too much moisture moving it to a level above 18% and leading to spoilage. Using the dew to bring moisture up is therefore sometimes limited to a short period of time. And sometimes, especially in windy conditions, the dew does not occur and add moisture to the alfalfa hay at all. Thus, a useful method of adding moisture to a windrow in a controlled fashion would provide a management tool for the producers of alfalfa.

Producers have attempted to add moisture by spraying water over the windrow. Normally this technique will add the required moisture to only the outside portion of the windrow and a majority of the alfalfa hay will still remain dry and experience excess shatter.

In the Finney Patent (U.S. Pat. No. 6,233,408 B1), a device was disclosed to evenly spread moisture into the windrow. A series of spikes entering into the windrow evenly distributed moisture in the way that natural dew introduces moisture into the windrow. Under conditions of low evaporation, the device works very well letting the moisture added to the windrow soak into the alfalfa over a one-half hour to one hour period. This relatively slow soak was due to the properties of alfalfa which is naturally coated with an outside waxy layer that was there to protect the plant for excessive evaporation when it was in its growth stage. However, when moisture is re-introduced at the point of harvest with the device disclosed by Finney, the outside waxy coating slows the soaking in of added moisture. When the conditions of higher evaporation are present, the moisture added by Finney will evaporate before it has a chance to soak into the alfalfa. The device disclosed by Finney also limits speed of treatment in that when travelling too fast, the spikes themselves shattered the alfalfa leaves and there is not a means for selecting levels of the windrow for treatment.

In the Staheli Patent (U.S. Pat. No. 6,109,008), moisture is added in the form of steam. The steam is very effective in penetrating thru the outside waxy coating. However, the steam is very volatile and the preferred method of application requires it to be contained by applying it in an enclosed area of the alfalfa hay baler which does not eliminating some of the leaf shatter that occurs before the alfalfa hay reaches the enclosed area of the baler. Even with application of steam directed to the enclosed area of the baler, there is a significant loss of moisture due to the volatizing of water, requiring a need for a high level of over-application to offset the moisture loss. The associated costs of heating water to the level at which it becomes steam and the higher rates of flow required to offset the loss to volatilizing become factors in the process at using the device disclosed by Staheli.

In the present invention, water is heated to a level needed to penetrate the waxy coating of alfalfa. Combined with the device disclosed by Finney to evenly spread the moisture into the windrow, it provides for an effective method for adding moisture to a windrow of alfalfa. A device that can heat the water to the desired level and evenly spread into the windrow is pulled by a truck or tractor as a separate operation prior to passing through the field with the baler as a separate pass between 5 and 30 minutes prior to baling.

BRIEF SUMMARY OF THE INVENTION

The device and method that has been invented, sprays hot water in a fine mist into the inside and around the outside of a windrow of alfalfa hay laying in the field just prior to baling of the alfalfa hay. Multiple spikes attached to a rotating shaft or series of shafts traveling over the windrow, enter the windrow and spray hot water evenly through the entire windrow. Moisture is therefore spread throughout the windrow without adding areas of higher and lower concentration of moisture as happens when moisture is sprayed over the top of the windrow. The effect of dew condensing into and on a windrow of alfalfa hay is therefore closely duplicated with the method and device. In this new invention, heat is applied to the water being sprayed providing for rapid penetration into the alfalfa so that evaporation of the added water before it soaks into the alfalfa hay is minimized. In dry areas of alfalfa hay production, where the condensation of dew is relied upon to bring moisture into windrowed alfalfa hay for harvest, this method provides an alternative for preparing alfalfa hay for baling.

In one aspect the invention provides an apparatus and method for simulating the effects of dew including a moveable platform; a rotatable base, the rotatable base being connected to the platform; and a plurality of elongated rods for penetrating and spraying beneath the surface of a windrow, the rods radiating from a longitudinal axis of the rotatable base.

BRIEF DESCRIPTION OF THE SEVERAL VIEWS OF THE DRAWING

FIG. 4 is a cross section diagram of the action of the cam mechanism.

DETAILED DESCRIPTION

Figure 1:
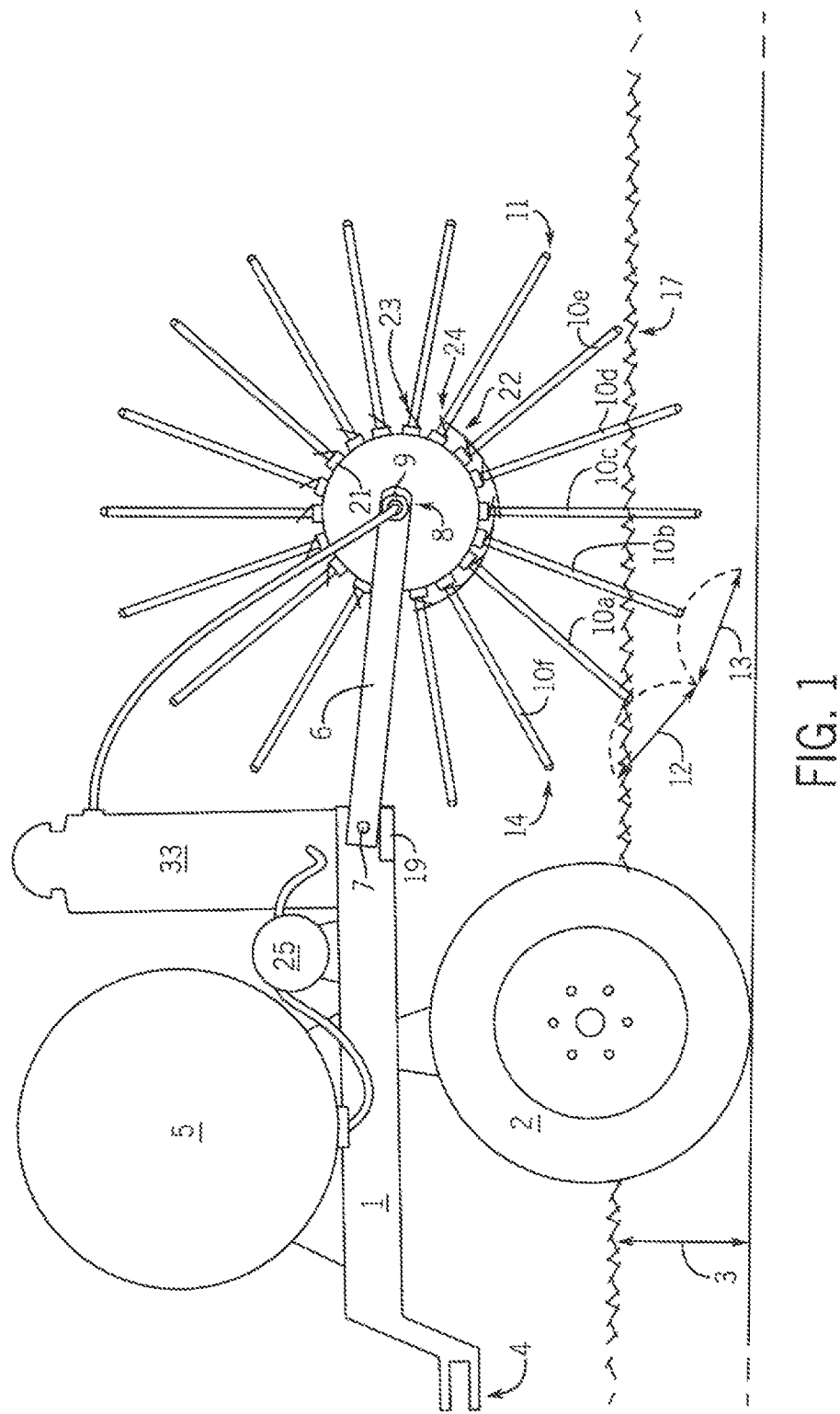
FIG. 1 is a side view of the complete device.

In FIG. 1, a frame 1 is designed to hold a device supported on wheels 2 that straddle the windrow being treated 3. The frame setup in this fashion can be pulled from hitch point 4, by a tractor operating a separate pass before baling. A tank 5 to supply water is located on the frame 1 in a position to attain the maximum support. Alternatively a separate tank can be pulled behind or to the side of the device. Moisture is added at a rate of 5 to 20 gallons per ton of alfalfa hay to increase the moisture content. Depending on the number of acres to be treated and the availability of refill, the tank is sized between 100 and 2000 gallons. One or more pivot arms 6 are attached to the frame 1 with a free-moving swivel 7, allowing the arms to travel up and down. A hub is attached to the other end of the pivot arms 6 to holds a horizontal shafts 9 that are located at a distance sufficient to carry the shaft across the width of a windrow normally between 36 and 60 inches. The shaft 9 rotates freely in the hub 8 by means of a bearing or bushing. The shaft is hollow to allow for water to be conveyed through it or alternatively a separate water line may be attached to the outside of the shaft. Attached to the shaft 9 are multiple rods 10 that are referred to as spikes and together form what is referred to as a reel. The spikes are of a length sufficient enough to extend from the shaft 9 to within an inch of the ground, usually between 10 and 30 inches long. The spikes are hollow to convey the water or a separate water line can be attached to the outside of the spikes. The spikes 10 are fitted with a spray orifice 11 at the end. Water is delivered to the orifice 11 at a pressure great enough from pump 25 to create a fine mist with water droplets between 20 and 100 microns so that when the spikes are inserted into the windrow and moisture of the alfalfa is evenly brought up. Depending on the size of the outlet opening in the orifice, the pressure required to attain the desired micron size is between 200 and 700 psi. Delivering water to the orifice at pressures above 700 psi breaks the droplets into too fine of a mist causing drift of part of the applied moisture and reduced effectiveness. At the pressure selected, the orifices 11 delivers spray in a wide horizontal pattern 12 usually between 3 and 12 inches so that delivery just barely overlaps from the pattern from the adjacent spike 13. Spikes are spaced longitudinally on the shaft 9 in the same fashion, so that on a shaft 60 inches long, with spray orifices providing a 12 inch spray pattern there will be 6 spikes in each row. In this example, if the spikes were 18 inches long, the total diameter of the rotating reel would be 48 inches and its circumference would be 226 inches. In this example, with spray orifices providing a 12 inch spray pattern, there would be 18 spikes around the circumference of the reel in each of 6 rows providing for a total of 112 spikes to maintain the proper spacing. The spikes that are positioned such that in the lower radius of the groups of spikes are surrounded by the alfalfa hay in the windrow 3. As the device travels forward, the spikes within the windrow are held back by the alfalfa hay, causing the shaft 9 to rotate around the hub 8. The spikes entering the windrow will progressively penetrate the alfalfa hay as they travel on a radius around the shaft 9. The travel of the reel arm 6 is limited downward by a stop 19 which is adjustable so that the end of each spike comes between 1 and 4 inches of the ground.

In the preferred embodiment of the device and method provides for a means to turn off water flow to spikes not positioned in the windrow. As the shaft 9 rotates, the spikes are opened up to water flow from the position when they begin to enter the windrow 14 until they leave the windrow at position 17. A valve assembly 21 is positioned at the opening to each row of spikes. A trip mechanism 22 is positioned to open each valve for each row when it rotates to the beginning position 14 and then the trip mechanism holds the valve open until it reaches the exiting position 17. By opening the valve for spike 10f at position 14 just before that spike enters the windrow, the outside of the windrow will receive some moisture. To open the valve, and arm 23 is attached to each valve that operates the valve when depressed. This trip mechanism 22 depresses the valve and is normally constructed in an arc, located adjacent to arms that activate the valves 21. The trip mechanism is constructed in a fashion so the beginning and ending points of valve activation are movable to adjust for differing heights of windrows. Movement can be accomplished by using a sliding trip 24 on one or both ends of the arc.

Figure 2:
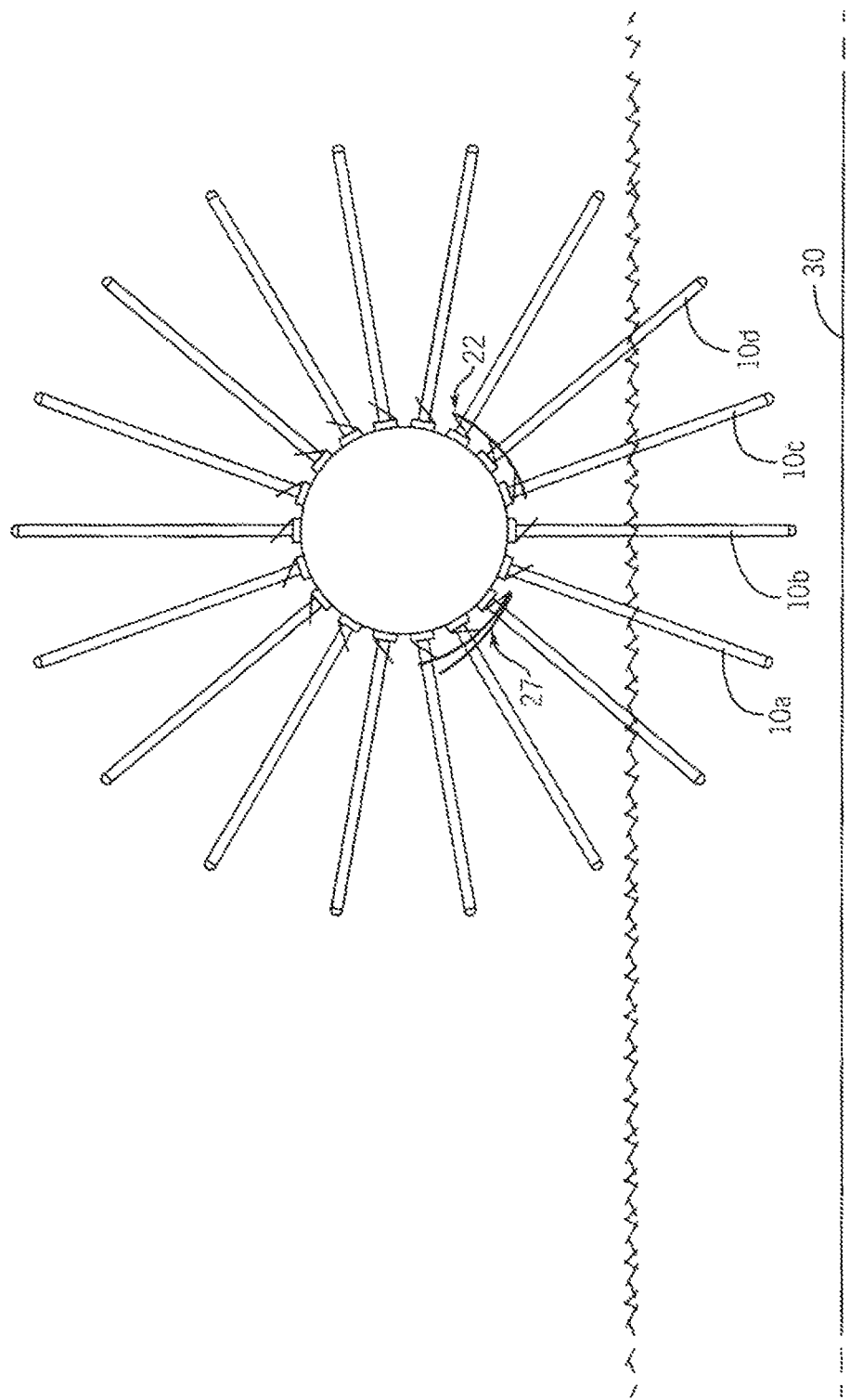
FIG. 2 is a side view of the reel with the section of the lower trip retracted to eliminate spray from the bottom of the windrow.

In some cases, the windrow 3 will have higher moisture in the lower part of the windrow due to transfer from higher moisture areas in the ground 30 in FIG. 2. Under these conditions, a center section 27 can be removed or slid away from the trip mechanism 22 so that the arm 23 will close the valve when travelling around the arc in the lower position and turn off spray from the spikes 10a and 10b.

Figure 3:
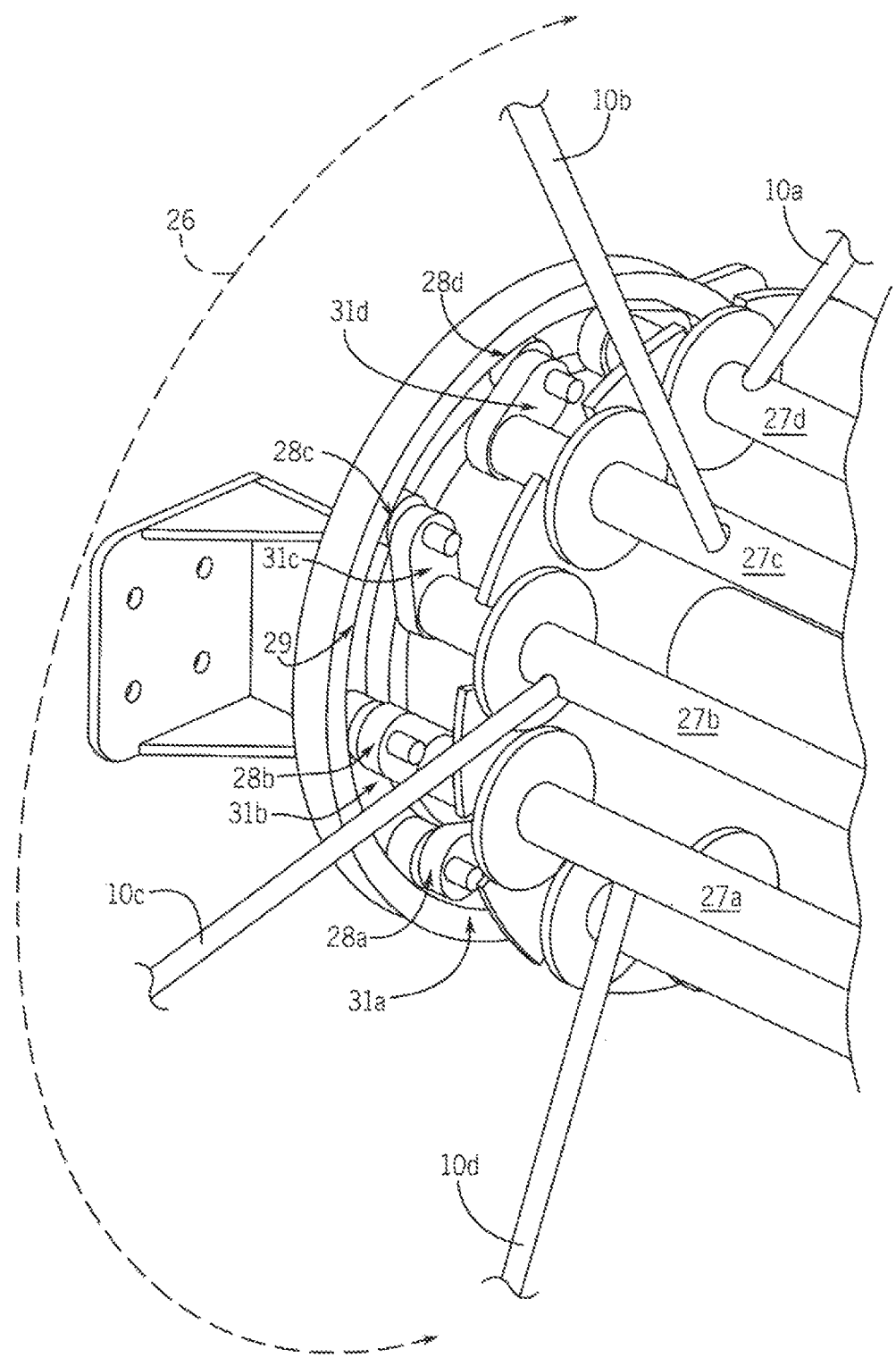
FIG. 3 is a perspective view of the cam mechanism improving the placement of the spikes.

To obtain maximum absorption of moisture and avoid evaporation the device should be able to travel at the same speed as the baler which will follow the device between 5 and 30 minutes after the device adds moisture to the windrow. When the spikes 10 in FIG. 3 are in the windrow, and travel around arc 26, they can move fast enough to disrupt the material in the windrow. When the device is moving at a speed greater that 2 miles per hour the spikes themselves separate leaves from stems in the alfalfa hay. To allow the device to move at speeds greater than 2 miles per hour and match the speed of the baler, the rows of spikes can be attached to separate cross shafts 27 taking the place of cross shaft 9. FIG. 1 and each cross shaft is rotated by the movement of a cam bearing 28 travelling in cam track 29. The cross shafts 27 are rigidly attached to a control arm 31 so that as the relationship of the cam bearing changes, the cross shaft rotates as seen in FIG. 4. The center point of the reel 32 is offset from the center point of the cam track 33 so that the action of the cam bearing 28 orients the spikes 10*a*, 10*b* and 10*c* to enter and exit the windrow 3 in a vertical orientation and avoid disrupting the windrow. Using the cam action also controls the spacing of the spikes 10 so that they are closer when positioned in the windrow reducing the number of rows of spikes required to maintain the spacing of the spray pattern 12 with the adjacent pattern 13. As seen in this example with an 18 inch spike and a spray pattern from the orifice 11 of 12 inches, the number of spikes required to cover the windrow is reduced from inches, the number of spikes required to cover the window is reduced from 112 to 60.

To have the water soak into the alfalfa quickly enough to avoid evaporation, the water is heated with a boiler 33 located on the frame 1 as seen in FIG. 1 between the pump 25 and the reel. Alternatively, the boiler can be located with a separate tank pulled behind or next to the device. The temperature of the water influences the amount of time needed to have the water soak into the alfalfa as follows:

| TEMPERATURE OF THE WATER | TIME REQUIRED TO SOAK INTO THE ALFALFA | PORTION OF THE WATER THAT WILL EVAPORATE INSTEAD OF SOAKING INTO THE ALFALFA |
|---|---|---|
| 140 degrees F. | 40 minutes | 50% |
| 150 degrees F. | 38 minutes | 40% |
| 160 degrees F. | 36 minutes | 35% |
| 170 degrees F. | 34 minutes | 30% |
| 180 degrees F. | 30 minutes | 25% |
| 200 degrees F. | 26 minutes | 20% |
| 210 degrees F. | 20 minutes | 15% |
| 220 degrees F. | 16 minutes | 10% |
| 240 degrees F. | 12 minutes | 5% |
| 260 degrees F. | 10 minutes | 5% |
| 280 degrees F. | 9 minutes | 5% |

Based on the cost of heating the water and the response, the optimum temperature range for heating is to deliver water between 180 degrees and 220 degrees.

The embodiments above are chosen, described and illustrated so that persons skilled in the art will be able to understand the invention and the manner and process of making and using it. The descriptions and the accompanying drawings should be interpreted in the illustrative and not the exhaustive or limited sense. The invention is not intended to be limited to the exact forms disclosed. While the application attempts to disclose all of the embodiments of the invention that are reasonably foreseeable, there may be unforeseeable insubstantial modifications that remain as equivalents. It should be understood by persons skilled in the art that there may be other embodiments than those disclosed which fall within the scope of the invention as defined by the claims. Where a claim, if any, is expressed as a means or step for performing a specified function it is intended that such claim be construed to cover the corresponding structure, material, or acts described in the specification and equivalents thereof, including both structural equivalents and equivalent structures, material-based equivalents and equivalent materials, and act-based equivalents and equivalent acts.

The invention claimed is:

1. An apparatus for adding heated water to hay in windrows and simulating the effects of dew thereto, comprising:
- a. a moveable platform; wherein the platform supports the following sub-parts:
  - i. a reservoir which holds water;
  - ii. a pressurizer, connected to the reservoir, which pressurizes the water to between 200 and 700 psi; and
  - iii. a heater, connected to the pressurizer, which heats the pressurized water to between 140 and 280 degrees Fahrenheit, to generate liquid pressurized heated water without generating steam;
- b. a rotatable base, the rotatable base being connected to the platform and communicatively connected to the heater to receive the liquid pressurized heated water without steam; and
- c. a plurality of elongated rods radiating from a rotational axis of the rotatable base, the rods being communicatively connected to the rotatable base to receive the liquid pressurized heated water without steam, the rods penetrating a top surface of a windrow and spraying the liquid pressurized heated water, without steam, from the rods beneath a top surface of the windrow.

2. The apparatus of claim 1, wherein the platform is supported on a wheeled axle that has a width between 36 and 60 inches to extend across a hay windrow.

3. The apparatus of claim 2, wherein the platform is a wheeled frame adapted to be pulled by a tractor.

4. The apparatus of claim 1, wherein the platform is arranged in front of the rotatable base.

5. The apparatus of claim 1, wherein the rotatable base rotates around a rotational axis which is adapted to be oriented parallel to the surface of a hay field over which the apparatus is to be used, the rotatable base further being constructed and arranged to be vertically pivotally coupled to the platform whereby a depth of penetration of a top surface of the windrow is controllable.

6. The apparatus of claim 1, wherein the rotatable base is constructed of a metal alloy.

7. The apparatus of claim 1, wherein the rotatable base is reel-shaped.

8. The apparatus of claim 1, wherein the rotatable base includes the following sub-parts:
- i. at least one shaft;
- ii. a pair of hubs; and
- iii. a cam mechanism;

to rotationally move the elongated rods.

9. The apparatus of claim 1, wherein the rods are disposed and evenly spaced about the periphery of the rotatable base.

10. The apparatus of claim 1, wherein the rods are spikes.

11. The apparatus of claim 1, wherein a distal end of each rod of the plurality of rods includes a spray orifice.

12. The apparatus of claim 1, wherein the rotating base and the rods cooperate by transmitting water from the reservoir to the spray orifice.

13. A mechanical spraying apparatus for spraying heated liquid water directly on alfalfa hay in windrows, simulating the effects of dew on the hay windrow, in varying evaporation conditions, prior to baling, comprising:

a. a moveable platform; wherein the platform supports the following sub-parts:
  i. a reservoir which holds water;
  ii. a pump communicatively connected to the reservoir and which pressurizes water to a predetermined pressure between 200 and 700 psi; and
  iii. a heater communicatively connected to the pump which heats the pressurized water to a predetermined temperature between 180 and 220 degrees Fahrenheit to generate pressurized heated liquid water, without generating steam;
b. a rotatable base, the rotatable base being connected to the platform and communicatively connected to the heater to receive the liquid pressurized heated water without steam; wherein the rotatable base includes the following sub-parts:
  i. a plurality of cross-shafts arranged in parallel with each other and in a cylindrical configuration about a central axis;
  ii. a pair of hubs disposed at opposite ends of the central axis; and
  iii. a cam mechanism communicatively connected to the cross-shafts; wherein the rotatable base rotates around the central axis which is adapted to be oriented parallel to the surface of a hay field over which the apparatus is to be used, the rotatable base further being constructed and arranged to be vertically pivotally coupled to the platform whereby a depth of penetration of a top surface of the windrow is controllable; and
c. a plurality of elongated rods communicatively connected to the heater and the rotatable base to receive the liquid pressurized heated water without steam, for penetrating a top surface of a windrow and spraying the pressurized heated liquid water, without steam, from the rods beneath a top surface of the windrow, the rods radiating from the central axis of the rotatable base and being communicatively connected to the heater, to rotationally move the elongated rods.

* * * * *